United States Patent
Hering et al.

(10) Patent No.: US 7,811,265 B2
(45) Date of Patent: Oct. 12, 2010

(54) ULTRASONIC PROBE WITH POSITIONING DEVICE FOR EXAMINATION DEVICES AND OPERATION DEVICES

(75) Inventors: Steffen Hering, Hall (AT); Rainer Marksteiner, Schwaz (AT); Hannes Strasser, Hall (AT)

(73) Assignee: Innovacell Biotechnologie GmbH, Innsbruck (AT)

( * ) Notice: Subject to any disclaimer, the term of this patent is extended or adjusted under 35 U.S.C. 154(b) by 984 days.

(21) Appl. No.: 10/432,642

(22) PCT Filed: Nov. 21, 2001

(86) PCT No.: PCT/EP01/13535

§ 371 (c)(1),
(2), (4) Date: Nov. 12, 2003

(87) PCT Pub. No.: WO02/45588

PCT Pub. Date: Jun. 13, 2002

(65) Prior Publication Data

US 2004/0092821 A1 May 13, 2004

(30) Foreign Application Priority Data

Nov. 24, 2000 (DE) .................. 100 58 370
Jul. 18, 2001 (DE) .................. 101 34 911

(51) Int. Cl.
*A61M 5/00* (2006.01)
(52) U.S. Cl. .................. 604/264; 604/116; 604/117; 600/464; 600/461; 600/459; 600/407
(58) Field of Classification Search ......... 604/116–117, 604/264; 600/459, 461, 464
See application file for complete search history.

(56) References Cited

U.S. PATENT DOCUMENTS

| 4,363,326 A | 12/1982 | Kopel |
| 4,402,324 A | 9/1983 | Lindgren et al. |
| 4,489,730 A | 12/1984 | Jingu |
| 4,542,747 A | 9/1985 | Zurinski et al. |
| 4,635,644 A | 1/1987 | Yagata |
| 4,742,829 A | 5/1988 | Law et al. |

(Continued)

FOREIGN PATENT DOCUMENTS

DE  3 618 906 C2  12/1986

(Continued)

OTHER PUBLICATIONS

Hari Ponnekanti et al., "Fundamental Mechanical Limitations on the Visualization of Elasticity Contrasts in Elastography," Ultrasound in Medicine & Biology, vol. 21, Issue 4, 1995, pp. 533-543 (Abstract only).

(Continued)

*Primary Examiner*—Brian Casler
*Assistant Examiner*—John F Ramirez
(74) *Attorney, Agent, or Firm*—Duane Morris LLP (57) ABSTRACT

An ultrasonic probe with an ultrasonic head (K), which is arranged on or in a shaft (S) and is moveable with or in this shaft, and a positioning apparatus (P) for at least one examination or operating device is described, which is connected with the shaft. Also, medical operating apparatuses with examination probes and uses of the ultrasonic probe and the medical implements are described.

21 Claims, 4 Drawing Sheets

U.S. PATENT DOCUMENTS

| | | | |
|---|---|---|---|
| 4,763,662 A * | 8/1988 | Yokoi | 600/461 |
| 4,869,258 A | 9/1989 | Hetz | |
| 4,877,033 A | 10/1989 | Seitz, Jr. | |
| 4,883,059 A | 11/1989 | Stedman et al. | |
| 4,911,173 A * | 3/1990 | Terwilliger | 600/464 |
| 4,974,931 A * | 12/1990 | Poole | 385/28 |
| 5,052,396 A | 10/1991 | Wedel et al. | |
| 5,235,987 A | 8/1993 | Wolfe | |
| 5,343,865 A | 9/1994 | Gardineer et al. | |
| 5,419,777 A * | 5/1995 | Hofling | 604/264 |
| 5,469,853 A | 11/1995 | Law et al. | |
| 5,596,990 A * | 1/1997 | Yock et al. | 600/467 |
| 5,853,368 A * | 12/1998 | Solomon et al. | 600/439 |
| 5,924,992 A | 7/1999 | Park et al. | |
| 6,083,169 A | 7/2000 | Hansen | |
| 6,095,981 A | 8/2000 | McGahan | |
| 6,238,336 B1 * | 5/2001 | Ouchi | 600/160 |
| 6,248,076 B1 * | 6/2001 | White et al. | 600/463 |
| 6,261,234 B1 * | 7/2001 | Lin | 600/461 |
| 6,283,942 B1 * | 9/2001 | Staehlin et al. | 604/116 |
| 6,302,875 B1 * | 10/2001 | Makower et al. | 604/528 |
| 6,338,717 B1 | 1/2002 | Ouchi | |
| 6,368,280 B1 * | 4/2002 | Cermak et al. | 600/459 |
| 6,855,124 B1 * | 2/2005 | Gonzalez et al. | 604/96.01 |

FOREIGN PATENT DOCUMENTS

| | | |
|---|---|---|
| DE | 199 62 209 A1 | 6/2000 |
| DE | 101 19 522 A1 | 12/2002 |
| EP | 0 446 645 | 9/1991 |
| EP | 0446645 | 9/1991 |
| JP | A 11 244 289 | 9/1999 |
| WO | WO 96/32889 | 10/1996 |

OTHER PUBLICATIONS

T. Varghese et al., "Nonlinear Stress-Strain Relationships in Tissue and Their Effect on the Contrast-To-Noise Ration in Elastrograms," Ultrasound in Medicine & Biology, vol. 26, Issue 5, Jun. 2000, pp. 839-851 (Abstract only).

* cited by examiner

Transversal image

Longitudinal image

ULTRASONIC PROBE WITH POSITIONING DEVICE FOR EXAMINATION DEVICES AND OPERATION DEVICES

RELATED APPLICATIONS

This application is a U.S. national stage of PCT International Application Number PCT/EP01/13535, filed Nov. 21, 2001, claiming priority from German Patent Application No.DE 100 58 370.9, filed Nov. 24, 2000, and German Patent Application No.DE 101 34 911.4, filed Jul. 18, 2001, The invention relates to a positioning apparatus for insertion and positioning of an ultrasonic probe and a further examination or treatment device in an organism to be analyzed, and in particular, an endoluminal ultrasonic probe, which is equipped with a positioning apparatus, which is particularly equipped for guiding and positioning of a further examination or operating device in the body of the organism. The invention also relates to a method for arranging and/or actuation of examination or operating devices in the body and applications of examination probes, in particular, an endoluminal ultrasonic probe with a positioning apparatus.

Modern ultrasound apparatuses provide an important contribution for diagnostics that provide images and make possible a fast, painless, and safe analysis of organs and anatomical and pathological structures. In addition, sonographic technologies have been developed, with whose assistance it is possible to take ultrasound-specific biopsies or aspirate from organs or body cavities.

Since the beginning of the eighties, the first puncture aids for ultrasonic probes already have been described (see, for example, U.S. Pat. Nos. 4,363,326, 4,402,324, 4,489,730, 4,542,747, and 4,635,644). These devices operate as simple puncture guides for ultrasonic probes, with which biopsies specified by ultrasound can be taken from the body starting from the body surface. Also, puncture guides are known, which on one side, are fixedly integrated in the ultrasonic probe (U.S. Pat. Nos. 4,363,326 and 4,635,644) or are removable (U.S. Pat. No. 4,402,324). These removable puncture aids have different forms. Thus, among other things, a wedge-shaped puncture guide has been developed, which fits in a precisely adapted, wedge-shaped transverse recess in the ultrasonic probe (U.S. Pat. No. 4,489,730). After the puncture, the puncture needle can be withdrawn along with the puncture guide from the ultrasonic probe, so that the needle can be left in the body of the patient and the ultrasonic probe can be removed simultaneously. In U.S. Pat. No. 4,542,747, an ultrasonic probe is described, which comprises two halves, each with a guide slot. After assembly of the two halves, a puncture channel is formed by the two matched slots. After the puncture, the two ultrasonic probe halves can again be separated from one another and removed, so that, again, the needle can be left free in the patient. From U.S. Pat. No. 5,052,396, a removable puncture guide is known, which has multiple guide slots for receiving needles with different diameters.

Puncture aids for endoluminal ultrasonic probes are also known. Thus, a transvaginal ultrasound probe is known, on which a puncture guide has been transversely attached, so that with ultrasound selectively, egg cells can be removed from the ovaries or biopsies from the female pelvic organs (U.S. Pat. No. 4,742,829). For improved representation of the puncture needle in the ultrasonic image, in addition to normal sonographic technology, also a vibration system has been developed, which excite the puncture needle in subtle oscillations, whereby the needle, based on the Doppler effect, can be better illustrated (U.S. Pat. No. 5,343,865). In addition, also flexible endoluminal ultrasonic probes with a working channel are known, which are not impaired by bending of the ultrasonic probe (U.S. Pat. No. 5,469,853). With this system, biopsies in the frame of endosurgical instruments can be taken. Also surgical instruments are used, with which the tissue to be treated can be analyzed in advance before the incision or coagulation with the sonic head of the apparatus.

In the last years, the described types of puncture aids have been further simplified and improved. Thus, shell-shaped guides are known, which only insignificantly enlarge the diameter of the ultrasonic probe (U.S. Pat. No. 5,924,992). In addition, retaining systems of the puncture guides are known, which make possible a removal of the inserted needle from the sonic probe with endoluminal ultrasonic probes, so that the ultrasonic probes can be removed and the puncture channel can be left in the patient (U.S. Pat. No. 6,095,981).

The conventional ultrasonic probes with puncture aids have a series of disadvantages. The function of the known arrangements is limited, in that the distance of an inserted diagnostic or operating device (for example, a needle) from the sonic head is fixed and can neither be changed or exactly controlled in the ultrasonic image. None of the described puncture systems for ultrasonic probes is controllable, such that the distance from the inserted implement to the sonic head with the predetermined position of the endoluminal sonic probe in the patients can be manipulated. Therefore, with the present ultrasonic probes and the puncture systems connected with them, it is impossible to place catheters, puncture needles, or other examination or operating devices specified with the aid of an endoluminal sonic probe and at variable distance from the sonic head in the surrounding tissue of vessels or narrow hollow organs. This is true because the position of the ultrasonic probe would have to be manipulated, such that the hollow organ or the vessel in which the probe is located would be harmed (for example, ripped, torn, pinched, perforated), or because this manipulation is very inhibited by the structure of the surrounding environment. An endoluminal ultrasonic probe can be shifted in this case only in the longitudinal axis or rotated about this axis.

With the ultrasonic probes with the puncture aids described in the prior art, the accurate puncture of a structure, which is located transversely in a wall region of a narrow lumen (for example, the urethra or a blood vessel), is not possible, due to the lack of changeability of the exit angle of the diagnostic or operating device from the puncture device. In addition, the puncture guides up to this point cannot be selectively shifted along the shaft of the endoluminal sonic probe. These disadvantages are also true for common endoluminal MRI probes.

It is further generally known that the inspection of the urethra and the injection of fillers ("bulking agents") until now take place predominately with the aid of endoscopes. In order to avoid damage upon insertion of the endoscope (in particular, the mucous lining and the layers lying there under), endoscopes of this type are generally equipped with a perfusion channel, which discharges on the front side of the endoscope. By means of the continual flushing of the urethra with fluid, the urethra is widened in front of the endoscope lens. In this manner, the endoscope can be inserted, without perforating the urethra wall. The progression and the lumen of the urethra are visible by the widening before the endoscope in its course. At the same time, by application of liquid in the urethra during the therapy, the therapy result can be determined.

Common constructions of transluminal ultrasonic probes are useable for the application of bulking agents in the urethra in a restricted manner only, since upon insertion of the probe in the urethra by unpracticed operators, injuries can occur.

With transurethral sonic probes with only one sonic plane (that is, probes which only provide the representation of the transverse (cross sectional) image of the tube), therefore, frequently, an endoscope device also is necessary for the risk-free insertion of the probe into the urethra.

By the introduction of a second sonic plane in the sonic head of a transluminal sonic probe, in addition to the detection of the cross section of the urethra, a longitudinal sectional image of the urethra is produced and therewith, the longitudinal representation of the urethra (that is, in its longitudinal progression) with an endoluminal sonic probe is possible. These types of probes, however, have the disadvantage that upon insertion into the lumen, it lies directly on the urethra on its inner wall and the operator is unable to see the longitudinal view in the lumen of the urethra. Since the urethra is not filled with fluid, serious injuries can take place upon insertion of the probe (in particular, with men).

With trans-rectal sonic probes, balloon constructions in the vicinity of the sonic head are known, which are filled for widening of the rectum, whereby access into the lumen is improved. These embodiments of transluminal probes are not suited for analysis of particularly narrow urethras, however, since they do not have a perfusion channel for widening of the lumen by a spraying process of the channel.

A further disadvantage of conventional constructions of ultrasonic probes with manipulators is their complicated structures. Conventional manipulators are equipped with a micro-mechanism, and therefore, are expensive and complex to manufacture. A one-way use is not practical with micro-mechanical manipulators.

Also, flexible ultrasonic probes and endoscope devices are known, which are equipped with deflecting devices. A conventional deflecting device, for example, is made available by a linkage, which is integrated in the probe shaft and with its help, the ultrasound head can be deflected.

The object of the present invention is to provide an improved ultrasonic probe with a positioning device, with which the disadvantages of the conventional arrangements can be overcome and which, in particular, has a broadened application range. With the present invention, in particular, a precise monitoring of the positioning of the diagnostic or operating devices in the body of an organism should be possible. A further object of the invention is the provision of a positioning device, which is suited for the insertion and positioning of examination probes in organisms. The object of the invention is also to make available novel methods for positioning of diagnostic and operating devices and for application of diagnostic or operating devices.

The basic idea of the invention is to provide a positioning apparatus for at least one examination and operating device at an ultrasonic probe with an ultrasonic head, which is attached on a flexible or rigid shaft and is moveable with this shaft, whereby the positioning apparatus has at least one puncture guide, which forms a guide with a defined mounting or a stop for the examination or operating device, and the examination and operating device is displaceable with a deflecting device, such that the stop (or a lumen of the puncture guide, an exit opening of the lumen, or the examination or operating device inserted in the lumen in an operating state) has a predetermined, or temporally changeable, position relative to the ultrasonic head. The ultrasonic probe preferably is an endoluminal ultrasonic probe. The examination or operating device (below: manipulation device) is, for example, a biopsy device, an injection pipette, or a surgical apparatus.

The ultrasonic probe of the present invention has the advantage that the positioning apparatus for the manipulation device simultaneously forms a defined mounting and makes possible a flexible adjustability (displaceability, angle adjustment) into predetermined positions.

With the ultrasonic probe with a flexible puncture aid, for the first time it is possible to selectively change the distance between the sonic head and the inserted manipulation device, which, for example, exits transversely to the ultrasonic probe from the guide device. This characteristic brings different advantages, in particular, with use in hollow organs, vessels, joints, other body cavities or narrow operating areas, in which the ultrasonic probe practically can be rotated, displaced forward, or displaced backward only. By the application of an endoluminal ultrasonic probe with a flexible puncture aid, the position of the operating or diagnostic device (for example, a catheter) can be changed selectively for the first time during the examination or operation.

According to a preferred embodiment of the invention, the deflecting device for the at least one manipulating device is adjustable with a control device. The deflecting device is driven, such that the stop of the puncture guide or the inserted manipulation device has a predetermined position relative to the ultrasonic head or is moved along a predetermined distance relative to the ultrasonic head. The position is represented by predetermined spatial coordinates relative to the ultrasonic head. The control device preferably is connected with the image-generating system of the ultrasonic probe via a coordinate generator. This contains, in particular, a display screen for displaying ultrasonic images. According to the present invention, it is provided that with the coordinate transmitter of the control device, signals corresponding to the adjusted relative coordinates of the puncture guide are transferred to the image-generating system and are used for displaying a marking, for example, a puncture aid line or a puncture aid point, on the display device.

One subject of the invention, therefore, is also ultrasonic probes with an image-generating system, which is connected with the control device of a puncture guide and is arranged for indicating the position of the puncture guide or the manipulation device inserted in the puncture guide on a display device, and a method for controlling a positioning device of an ultrasonic probe, in which the actual orientation and/or movement of a positioning device relative to the ultrasonic head is imaged on the display device of the image-generating system.

The puncture aid marking on the display device (for example, a puncture aid line or a puncture aid point) offers the possibility that before the exit of the manipulation device or implement from the working channel (lumen) of the puncture guide the exact end position in the ultrasound image can be calculated, and the puncture, for example, along the calculated puncture aid line in the ultrasound image, also can be monitored. After the advancement of the respective implement, its position can be controlled actually in a real-time ultrasound image and the application can be monitored. In addition to mono- or biplanar standard ultrasonic probes, also new ultrasonic technologies can be used, such as, for example, 3D-sonography or color Doppler sonography. With the assistance of various diagnostic- or operating devices, among other things, biopsies can be taken, medications, solutions or cell suspensions can be injected, via various working probes, energy applied, or surgical apparatus can be inserted and selectively placed and actuated.

According to a further embodiment of the invention, an endoluminal ultrasonic probe is provided, which with the diagnostic or operating device runs in the ultrasonic probe and through the ultrasonic head, so that with the assistance of the deflecting device the ultrasonic head and the diagnostic or operating device can simultaneously be selectively deflected.

These variations represent an important advancement, especially with laparoscopic ultrasound probes.

The position of a manipulation device, which can be inserted in the puncture guide, can be calculated before the exit from the puncture guide. The calculable position of the manipulation device after exit from the puncture guide is displayed in an ultrasonic image with the help of a puncture aid line or a puncture aid point. With the assistance of the coordinate transmitter, the puncture aid line or puncture aid point can be changed simultaneously with the deflecting or manipulation device and its position can be selected in a coordinated manner.

By means of the controllable deflecting device of the puncture guide of the ultrasonic probe, injection needles, for example, can be placed very precisely in hollow organs, vessels, joints, and body cavities. In this manner, for the first time, an exact and controllable injection of medications, cells, or therapeutic substances into the body of the patient is possible, whereby the location of the application of the examination or operating device can be changed and before the actual contact, can be exactly planned and selected. With this ultrasonic probe, all types of examination or operating devices can be inserted into the body of the patient ultrasound-specific through a working lumen of the puncture device, whereby this technology has all the advantages of minimally invasive surgery.

According to a further embodiment of the invention, an endoluminal ultrasonic probe with a biplanar standard ultrasonic probe is provided, which, in addition to the above-described injection devices, has a perfusion channel or a removable perfusion catheter. With this embodiment, the detection of longitudinal sonic images is made possible advantageously.

According to a further embodiment, an ultrasonic probe according to the present invention is equipped with a pressure sensor. Such an endoluminal sonic probe permits not only the ultrasonic-specific injection of bulking agents into the wall, for example, of the urethra, but also the control of the urethra pressure profile (and therewith, the therapy result) with the same device during the therapy. The pressure sensor includes, for example, a known pressure measuring apparatus (for example, with a membrane, which upon pressure changes, is deflected and transfers pressure changes, for example, via a fluid column to a transmitter), with which a pressure profile in a lumen, for example, the urethra, can be determined.

With the present invention, also a medical implement is made available, which forms a positioning apparatus for examination probes and further examination or manipulation devices. The positioning apparatus has a cylindrical working channel, preferably with an inner diameter in the range of 1 mm to 7 mm, for accommodating at least one examination probe (for example, an ultrasonic probe, endoscope device, and/or MRI probe). In the wall of the working channel, at least one further working channel is provided, in which the additional examination or treatment device can be inserted. The additional working channel also can be provided in an additional attachment sleeve that can be attached to the cylindrical working channel. The attachment sleeve also can support the deflecting device for the examination probe or the manipulation or examination device. The attachment sleeve, which forms a displaceable manipulation device, can be attached from the outside onto an endoscope, a zystoscope, or another examination apparatus.

In contrast to conventional medical implements, therefore, multiple functional advantages are achieved. First, the attachment sleeve with the manipulation device can be easily manufactured (for example, in an injection molding method). Second, the attachment sleeve can be exchanged as a one-way material after each use. Finally, a perfusion channel or catheter can be provided in the attachment sleeve, which is a direct part of the one-way article. The sterility of the medical implement is improved in comparison with conventional devices, in which the perfusion channel runs in the interior and after each use, must be sterilized.

A subject of the present invention is also a method for analysis and/or treatment of tissue or organs with the ultrasonic probe of the present invention. This can take place with or without use of the puncture aid marking on the display device.

According to a preferred embodiment of the method of the present invention, the ultrasonic probe is positioned first according to the application on or in the tissue or organ of interest. Next, an actuation of the positioning apparatus takes place, such that the puncture guide takes up predetermined relative coordinates relative to the ultrasonic head. Then, the respective manipulation device (examination or operating device) is inserted into the positioning apparatus and is moved to the stop and actuated in this operating position. In the operating position, possibly a movement of the manipulation device along the puncture aid marking is provided. This movement is controlled with the control device.

Important steps of the method of the present invention for positioning of examination or operating devices are the placement of the probe in the body with a determination of the tissue to be analyzed or operated on, the orientation of the positioning apparatus and the insertion and possibly actuation of the examination or operating device.

The subject matter of the present invention also is a method for injection of living cells in a carrier medium and/or biomaterials or biocompatible substances into an organism, whereby the ultrasound probe according to the present invention is used.

The invention is described with reference to a probe with an ultrasound head; however, it is not limited to this application. Alternatively, the probe can be equipped with all of the described embodiments with a so-called MRI head, such as is known for magnet resonance formation (MRI, magnetic resonance imaging).

Details and further advantages of the invention are described in the following description with reference to the attached drawings. In the drawings.

The invention represents a controllable ultrasound diagnostic and operating apparatus, with which, for the first time, diagnostic and operating devices can be inserted ultrasound-specific at a changeable angle relative to the axis of the sonic probe in an ultrasonic head and in a calculable distance from the sonic head in tissue. An essential advantage of the construction of the present invention in comparison to apparatuses known until now is that with a predetermined position of the ultrasonic probe, a manipulation device inserted in the puncture guide can be placed in an arbitrarily selectable distance from the sonic head of the ultrasonic probe. The novel puncture guide operates together with at least one deflecting device, which can be manipulated by a control device, such that the puncture guide and/or a manipulation device inserted in it can be deflected or shifted along the ultrasonic probe.

At the same time, with the assistance of a mathematical calculation, the position of the manipulation device, which can be inserted in the puncture guide, can be calculated before exit from the puncture guide and the calculated end position of the manipulation device can be represented before exit from the puncture guide in the display of the ultrasonic image as puncture aid line or puncture aid point. Thus, before the actual contact of the analyzer or operator, the entry angle and the end position of the examination or operating device can be predicted and can be selected with the control device during the contact. The application of the examination or operating device (for example, the insertion of a needle) can be controlled accurately, then, in a real-time ultrasonic image.

The invention is described next with reference to preferred embodiments, in which the ultrasonic probe has an ultrasonic head K, which is attached on the end of a shaft S and with this, is manually moveable, whereby the positioning apparatus P is arranged on or in the shaft S. The realization of the invention is not limited to this form. Alternatively, the positioning apparatus can be arranged with the adjustable puncture guide also directly on the ultrasonic head K or on the handle G.

In the figures, details of the positioning apparatus and the formation of the puncture aid marking merely are illustrated. The features of an ultrasonic probe with a handle, a shaft, and the ultrasonic head are known as such and therefore are not described likewise like details of the image-generating system.

Figure 1:
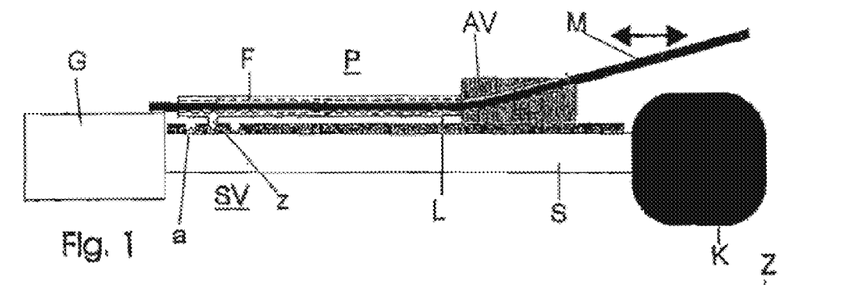
FIGS. 1 through 4 show schematic, partial sectional views of embodiments of ultrasound probes according to the invention.

A first embodiment of the ultrasonic probe with the handle G, the shaft S, and the sonic head K is schematically illustrated in FIG. 1. The positioning apparatus is mounted on the shaft S and is formed by the puncture guide F and the deflecting device AV. The puncture guide contains as a guide a tube- or slot-shaped lumen L, which penetrates the puncture guide F and the deflecting device AV as a working channel. In the deflecting device AV, the working channel is adjustable in its orientation relative to the probe. The puncture guide F and the deflecting device AV form a longitudinally extending component, which runs parallel to the axis of the shaft S. In the deflecting device AV, a predetermined angle of the working channel or lumen relative to the shaft axis is predetermined. The deflecting device AV and the puncture guide F can be displaced selectively with the assistance of the control device SV along the shaft S of the sonic probe. In this manner, the distance of the manipulating device M, which is located in the working lumen L, from the sonic head K changes. The displacement can take place discretely or in a continuous arrestable manner. The control device has a pin Z in the puncture guide F for discrete arresting in the illustrated embodiment, which precisely fits in one of a plurality of recesses of the sonic probe. The puncture guide F is flexible, so that it can be easily lifted or pivoted away from the shaft and displaced with the deflecting device and newly positioned. The position of the puncture guide F, the deflecting device AV, and the inserted manipulation device M correlates after the engagement of the pin of the puncture guide F with the corresponding puncture aid lines or puncture aid points in the ultrasonic image of the display device. The manipulation device M runs in the lumen L, which, for example, is a puncture needle or a catheter.

For continual arresting, instead of the pin, a suitable, releasable connection, for example, a clamping ring, can be provided.

The ultrasonic head K is structured in a known manner and contains, depending on the use, one or more sonic transducers (transducer elements) for sending or receiving ultrasonic waves. The ultrasonic head K can be arranged for generation of uniplanar or biplanar real-time ultrasonic images or of Doppler, color Doppler, or 3D-ultrasonic images. The shaft S comprises a flexible or rigid material, depending on the use. The puncture guide F is correspondingly at least partially also flexible or rigidly formed. In the case of an endoluminal ultrasonic probe, the ultrasonic head K typically has a diameter of approximately 5 to 10 mm. The lumen L in the deflecting device AV has a curved course relative to the longitudinal axis of the shaft S. The end of the lumen L facing toward the ultrasonic head K forms with the shaft axis a predetermined, fixed deflecting angle, through which the slope of the manipulation device M relative to the shaft axis is adjusted. The movement of the deflecting device AV determined with the control device therefore makes possible an adjustment of the manipulation device M corresponding to the double arrow.

The puncture guide is fixedly connected with the shaft of the ultrasonic probe, but can be removed and exchanged.

Figure 2:
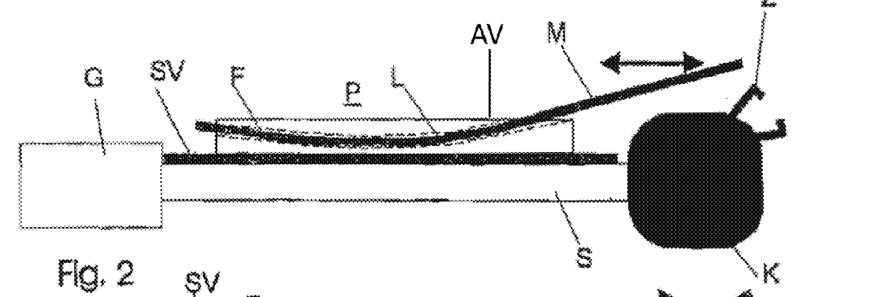

With the embodiment schematically shown in FIG. 2 of an ultrasonic probe, according to the invention, with the handle G, the shaft S, and the ultrasonic head K, the puncture guide F is mounted again transversely with the lumen L on the shaft S. The deflecting device AV coincides with the puncture guide F in this embodiment. The control device SV is formed by an axial actuator on the shaft S. In order to make possible an axial movement of the manipulation device M corresponding to the double arrow, the puncture guide F can be displaced axially parallel to the orientation of the shaft axis, so that the inserted manipulation device is also displaced. Therefore, again the distance of the manipulating device angularly exiting from the puncture guide to the ultrasonic head changes. Depending on the positioning of the deflecting device AV, the end of the manipulation device M has defined relative coordinates with reference to the ultrasonic head K.

By means of a defined adjustment of the deflecting device AV and/or puncture guide F, the manipulation device M is adjusted, so that its end has predetermined relative coordinates with reference to the ultrasonic head. This assumes that the insertion length of the manipulation device M is known or definitely adjusted. For adjustment of the insertion length, preferably a stop (not shown) is provided on the puncture guide or in the deflecting device AV, which cooperates with a corresponding projection on the manipulation device. The stop also can be provided on the handle or another part of the ultrasonic probe, or with the use of markings on the manipulation device M, with which the insertion length on the ultrasonic probe can be determined, the stop can be completely omitted.

In particular, when the shaft S is made from a flexible material, the ultrasonic head preferably is equipped with a clamping device for temporary fixing on the tissue to be analyzed. The clamping device, for example, is formed by a gripper Z actuable by the handle and makes it possible that the ultrasonic head before insertion of the manipulation device into the body is positioned. For fixing, also an inflatable balloon can be provided.

Figure 3:
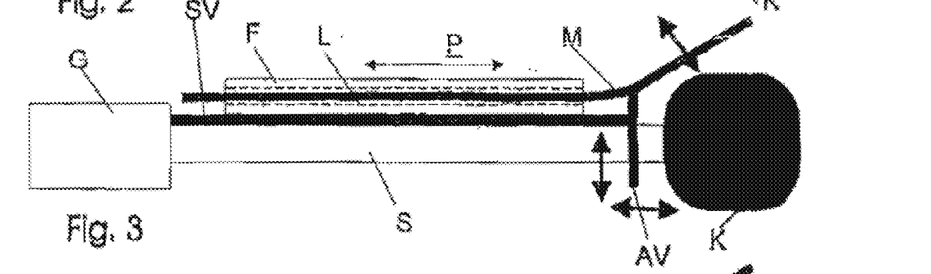

In FIG. 3, an endoluminal ultrasonic probe is schematically illustrated, in which the positioning apparatus contains the puncture guide F with the lumen L for receiving the manipulation device M and the deflecting device AV as separate components. The deflecting device is mounted on the shaft of the ultrasonic probe or on the sonic head. With the control device, the deflecting device is controlled such that the exit angle of a diagnostic or operating device in the puncture guide is changed after the exit from the puncture guide. The deflecting device can be moved in the longitudinal direction of the sonic probe or also at a right angle to it (see double arrows).

Figure 4:
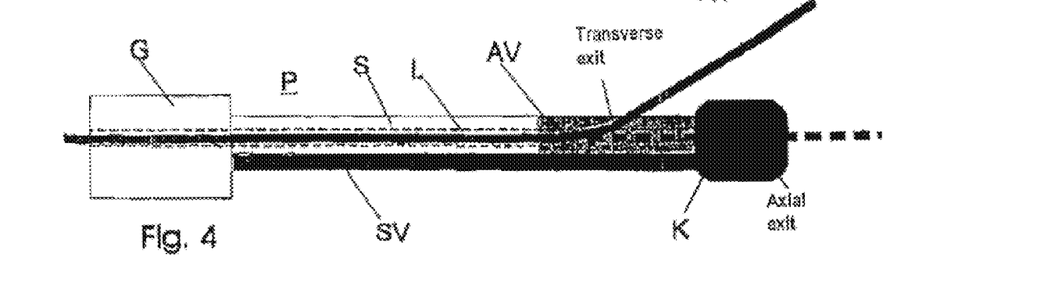

FIG. 4 shows a modified embodiment of the invention, in which the puncture guide is integrated in the shaft S of the ultrasonic probe. In the shaft S, the lumen L of the puncture guide runs near the signal lines of the ultrasonic head K. The deflecting device AV is arranged between the shaft S and the ultrasonic head K and is oriented for an inclined and/or axial exit of the manipulating device M. With the control device, the deflecting device AV can be actuated, in order to change the exit angle or the axial position of the manipulation device M.

For actuation of the deflecting device AV in the embodiments shown in FIGS. 1 through 4, either a mechanically, electromechanical, magneto-mechanical, or piezo-electric actuator can be used, or also a manual adjustments can be provided. Such actuators and adjustments are generally known, particularly from micro-surgery and laboratory technology.

Also, other deflecting devices can be used, which make possible a controlled and controllable transverse deflection of the manipulation device and which are controlled by the control device.

The manipulation device generally is an examination or operating device, such as, for example, a puncture needle, biopsy needle, injection needle, a catheter, or a micro-surgical tool. According to a particularly advantageous embodiment of the invention, the manipulation device includes a fluid supply device, a catheter, and an injection needle. With this construction, it is possible, with the supply device, to supply a medication, a solution, or a suspension with biological or biocompatible materials or suspended particles, such as, for example, living cells or implantation materials, via the catheter and the injection needle ultrasonic-selectively in a pre-determined tissue region or an organ. On the exit end of the lumen, a nozzle being integrated or attached as a component can be provided. The structure of the supply device, catheter, and injection needle can be equipped for injection of material under increased pressure (pressing in of so-called bulking agents).

A particular advantage of the present invention is that with a relative simply constructed deflecting device, with which the angle of the lumen is adjusted relative to the shaft, the inserted manipulation device can be reproducibly oriented. If the manipulation device is made of elastic stainless steel, for example, then this can be bend in the deflecting device, however, exits straight from the lumen.

According to a modified embodiment of the invention (not shown), multiple puncture guides can be provided on an ultrasonic probe, which are arranged for simultaneous guiding and positioning of multiple manipulation devices and whose position can be changed ultrasonically controlled. For example, multiple deflecting devices can provide multiple tube- or slit-shaped guide lumens on the shaft. Alternatively, these are integrated in the shaft.

The manipulation device can have also a gripper, a clamp, a tweezer, a cutter, and/or a knife as a surgical implement. For actuation of the manipulation device, this is connected with an external actuation device, if necessary. Also, an additional actuation device of the puncture guide can be provided, which is arranged for pivoting or shifting of the puncture guide on the shaft of the ultrasonic probe.

According to a further preferred embodiment of the invention, the ultrasonic probe is equipped with an endoscopy apparatus. The endoscopy apparatus is adjusted as the manipulation device with the puncture guide. Alternatively, the endoscopy apparatus is provided as a separate component on the ultrasonic probe. Finally, the manipulation device itself also can be formed by a probe with an ultrasonic head.

A particular advantage of the invention is that the puncture guide has a relative simple construction. This makes it possible that the handle, the shaft, the ultrasound head and/or the puncture guide are manufactured entirely or partially as one-way components.

An essential feature of the invention is that the manipulation device is positioned or moved with the puncture guide in a defined manner relative to the ultrasonic head. From the adjustment of the puncture guide and the geometric properties of the manipulation device, the relative coordinates relative to the ultrasonic head can be used for the inventive display of a puncture aid marking in an image-generating system of the ultrasonic probe. This is illustrated in FIGS. 5a and 5b.

Figure 5A:
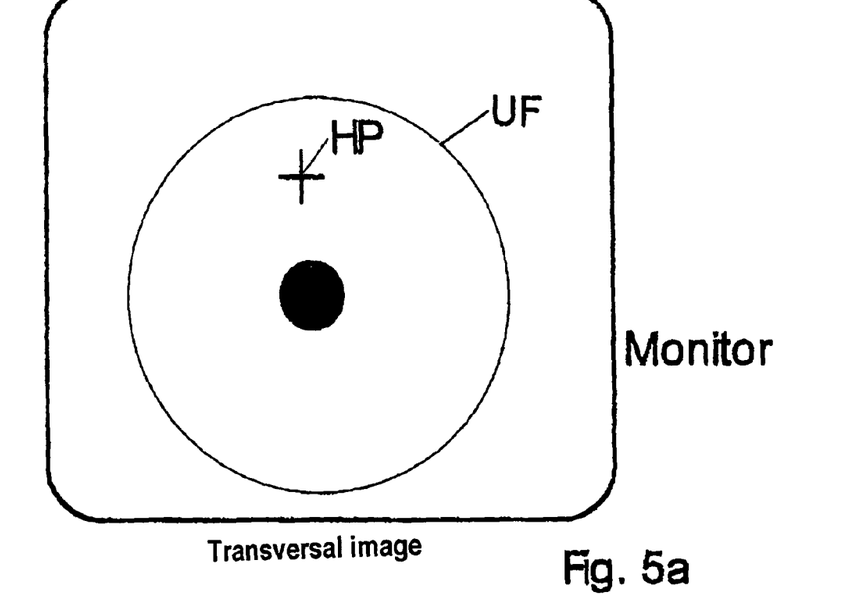
FIGS. 5a, 5b show schematic illustrations of the display of puncture air markings, according to the invention.
Figure 5B:
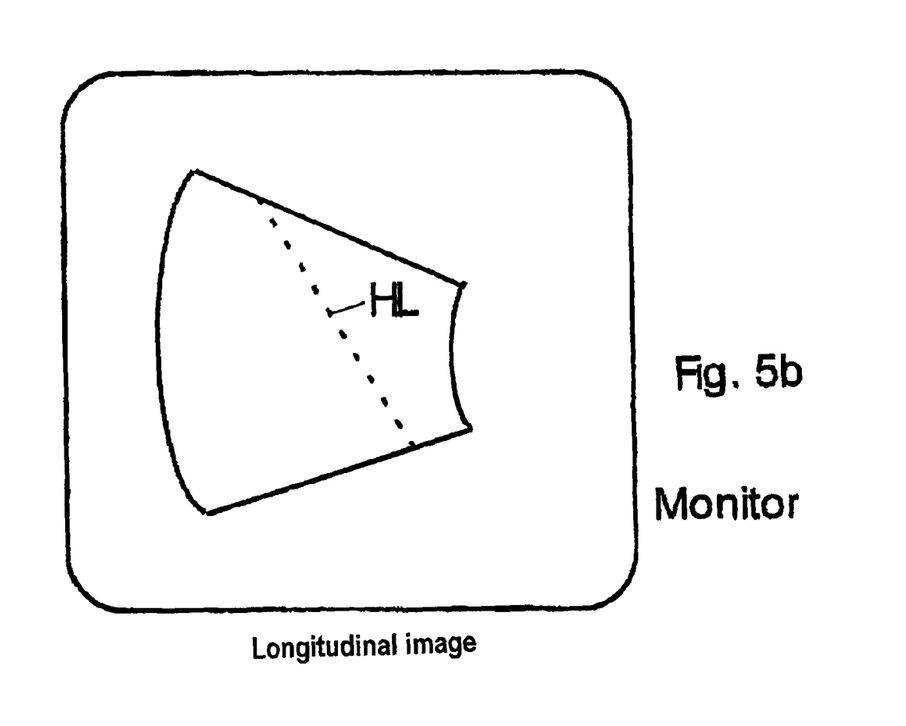

FIG. 5a shows a transversal image in a schematic illustration of a monitor M of the image-generating system, which is supplied from the endoluminal ultrasonic probe. In this image, a puncture aid point HP is formed as a puncture aid marking, which is produced from the coordinate transmitter of the control device for control of the deflecting device. The position of the puncture aid point HP relative to the ultrasonic field UF is adjusted on the monitor on the basis of position data, which the control device supplies corresponding to the actual orientation of the positioning apparatus. In this manner, the position of a diagnostic or operating device advanced in the puncture guide already can be recognized in the ultrasonic image before exit from the puncture guide and can be selectively changed. In FIG. 5b, a puncture aid line HL as the puncture aid marking is shown in a longitudinal image supplied from the ultrasonic probe. Again, the position of a diagnostic or operating device advanced in the puncture guide already can be recognized in the ultrasonic image before exit from the puncture guide and can be selectively changed. In addition, the advancement of the diagnostic or operating device can take place accurately in a real-time ultrasonic image. The puncture aid line HL also can mark a distance, which would cover the manipulation device inserted in the positioning apparatus in an advanced state with a corresponding actuation of the deflecting device.

The injection of living cells in a carrier medium and/or biomaterials or biocompatible substances in an organism, according to the present invention, includes the following steps.

The ultrasonic probe is inserted preferably in hollow organs, such as, for example, the gastro-intestinal tract, the urogenital tract, the nose and sinus cavities, airways, joints, body cavities, such as, for example, abdominal cavity, the chest cavity, the cranium cavity, the pelvic cavity, into a puncture channel, vessel or intra-operatively in an operating area. The insertion takes place alternatively with or without an introduced manipulation device, which here is an injection device. Subsequently, the positioning apparatus, if necessary, with the use of the puncture aid marking, is adjusted and, if necessary, the injection device is introduced. The injection device is connected with a reservoir of the substance to be injected. A preferred application is the injection of medications, fluids, solutions, suspensions with biological or biocompatible materials and/or suspensions with living cells, in particular, with or without carrier materials. A transurethral or transrectal injection for therapy of urinary incontinence or stool incontinence takes place, for example. In this connection, myoblasts, bulking agents, for example, collagen, pharmacological substances and/or growth factors are injected into the cell area of interest. The myoblasts are used alone or in combination with biocompatible materials (bulking agents) as material implants. The injection is monitored with ultrasonic control.

Figure 6:
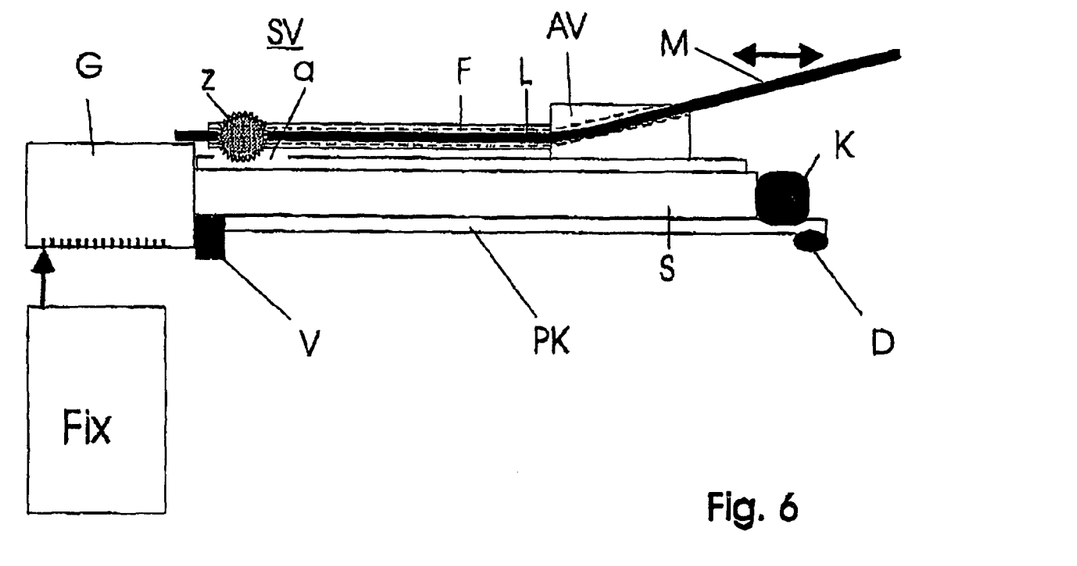
FIGS. 6 through 9 show further partial sectional views of embodiments of the ultrasonic probes, according to the invention.

FIG. 6 illustrates a further embodiment of the ultrasonic probe according to the present invention, which is equipped with a deflecting device AV for a manipulation device M corresponding to one of the above-described forms and which additionally has a perfusion channel (or perfusion catheter) PK. The components of the ultrasonic probe are designated with the same reference numerals as those used in FIGS. 1 through 4, so far as they are analogous to the above-name embodiments. The deflecting device AV is modified, such that the driving of the manipulation device M takes place with the use of a gear Z, which cooperates with a corresponding tooth distance a. The perfusion channel PK runs parallel to the shaft S. The free end of the perfusion channel PK is located in front of or near the ultrasonic head K and is formed, such that a perfusion liquid supplied from an external reservoir (not shown) exits in front of or near the sonic head in the respective investigated lumen, for example, the urethra in the direction of the bladder, so that the lumen can be rinsed with the perfusion fluid. With the perfusion fluid, the lumen is widened in front of the ultrasonic head K. The wall of the lumen, for example, the wall of the urethra, lifts off from the ultrasonic head K. As the ultrasonic head K, a biplanar sonic head is used, which is arranged for receiving ultrasonic images in two sonic planes. The first sonic plane serves for the transverse, radially directed observation of the lumen. The second sonic plane serves for the axial observation of the lumen. The second (or longitudinal) sonic plane makes possible an imaging of the space opened by the perfusion fluid in front of the sonic head. This represents a considerable advantage over conventional endoscopic apparatuses. The probe can be inserted risk-free into the lumen without use of an additional endoscope (like the type provided with the embodiment of FIG. 7, for example), in particular, into the urethra. The risk of injury with transurethral sonography is essentially reduced.

The perfusion channel PK is equipped on the opposite end with a valve V for connecting a fluid supply. The valve V preferably is actuated such that with the endoluminal sonic probe of the invention, the lumen of the urethra is filled with a permanent perfusion rinsing stream. With the embodiment of the ultrasonic probe with the perfusion channel PK, the ultrasonic probe represents an ultrasonic zystoscope.

The components "Fix" shown in FIG. 6 represent a fixed fix-unit, which serves for performing the pull-back technology which is known as such. With the sonic probe of the invention, with the pull-back method, the cross sectional ultrasonic image, upon pulling back (or analogously, upon advancement) of the sonic probe with the assistance of a planimetric calculation procedure can be added and thus, the entire urethra wall can be reconstructed three-dimensionally. Therefore, a measuring device with a sensor system (see scaling) is provided, which determines the relative coordinates of the sonic probe with reference to a fixed point Fix, which with the entire analysis is brought into its fixed position on the patient. With this sensor system, the advancement of the sonic probe into the urethra can be controlled and the relative coordinates can be transmitted into the calculating unit. From the individual cross sectional images, then, a three-dimensional model of the urethra is computed.

On the free end of the perfusion channel PK, a pressure sensor and/or an electrode device D is provided. Determining a pressure profile in a lumen, for example, the urethra, with a pressure measurer is known as such. According to the invention, however, this is performed with a particular advantage with the ultrasonic probe, which is equipped with the manipulation and, in particular, the injection device. Such an endoluminal sonic probe allows not only the ultrasonic-specific injection of filling agents into the wall of the urethra, rather also permits the control of the urethra pressure profile (and therewith, of the therapy results) with the same device during the therapy.

The electrode device includes, for example, a stimulating electrode D, which is localized in the direct area of the sonic head and enables the field stimulation of muscle fibers in the surrounding environment of the urethra and the determination of contractibility parameters in the ultrasonic image. It is known that electrical muscular activity can be measured with the assistance of electrodes, which lie on the upper surface of the fibers (electro-myogram). The transluminal ultrasonic probe of the invention, which is equipped with such an electrode D, makes possible the determination of electrical muscular activity simultaneously to the ultrasonic image. Thus, important parameters about the muscular function in the urethra can be obtained, particularly with the diagnostic of urinary incontinence.

With the assistance of the so-called ultrasonic elastography (see Ponnekanti et al in "Ultrasound in Med. Biol." vol. 21, 1995, pp. 533-543, and Varghese et al in "Ultrasound in Med. Biol.", vol. 21, 2000, pp. 533-543), the elasticity or rigidity of the tissue to be analyzed can be determined. With this method, a mechanical impulse is transmitted to the tissue to be analyzed with the aid of a movement element. This movement element can be a vibration device in the probe or also a displacement device, which is connected with a fix point "Fix", which is independent of the object (patient) to be analyzed. Before and after the defined mechanical compression of the tissue to be analyzed, parameters for rigidity or elasticity of the tissue are determined from the ultrasonic image.

In an advantageous embodiment of the sonic probe, the ultrasonic elastography is used for the diagnosis with urinary incontinence by measuring of the elasticity. The sonic probe shown in FIG. 6 is displaced in a defined manner with the ultrasonic elastography measurement, so that on the urethra wall, defined extension and relaxation forces are exerted. The reaction of the urethra wall to these mechanical forces can now be measured by the sonic probe and with the aid of ultrasonic elastography, can be quantified.

Figure 7:
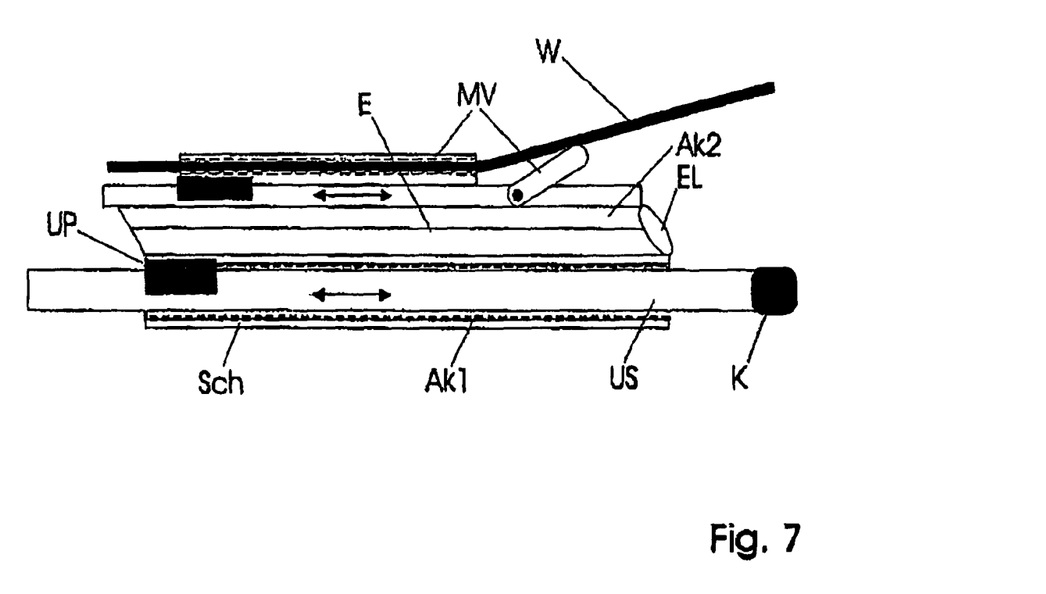

A further embodiment of a medical implement of the invention is shown in FIG. 7 in extracts. The implement can be used with particular advantage for injection of a suspension composition, which is described in the patent application DE 101 19 522.2 and whose disclosure content is included in the present patent application. The implement has a shaft Sch with at least two working channels AK1, AK2. In working channel AK1, an ultrasonic probe US with an ultrasonic head K is arranged. According to a preferred embodiment of the invention, the ultrasonic probe US is axially movable relative to the shaft Sch. A measuring device UP is provided on the shaft Sch, with which the position of the ultrasonic probe US in the working channel can be determined relative to the shat Sch. The position of the probe is detected, for example, by means of markings on the probe shaft. From the markings, coordinates are derived, which can then be used to combined longitudinal sections of the ultrasonic image to spatial images. In the second working channel AK2, an endoscope device E is arranged, on whose body-sided end, for example, an endoscope lens EL is provided for integrated illumination of the respective analyzed or treated tissue. The illumination takes place preferably over an angle range of 0 to 90°.

On the second working channel AK2 and/or the endoscope direction E, a manipulation device MV for actuation of a tool W is provided. The tool, for example, is a catheter or an injection needle. The actuation of the tool takes place in the above-described manner. The tool W, for example, is an injection needle, the part of the above-described mixing and application devices or the fluid supply devices.

The application of the implement according to FIG. 7 takes place, such that the implement first is brought into position in the body part to be treated (for example, hollow organ, tissue). With the endoscope device E, the tissue to be treated is visually observed. With a control device or with the use of ultrasonic control, the tool W is positioned. Next, the application of the suspension composition takes place via the tool W into the tissue area of interest, whereby the coordinates (in particular, end coordinates) are determined in the manner described above and the progress of the application is monitored with the ultrasonic probe US.

Figure 8:
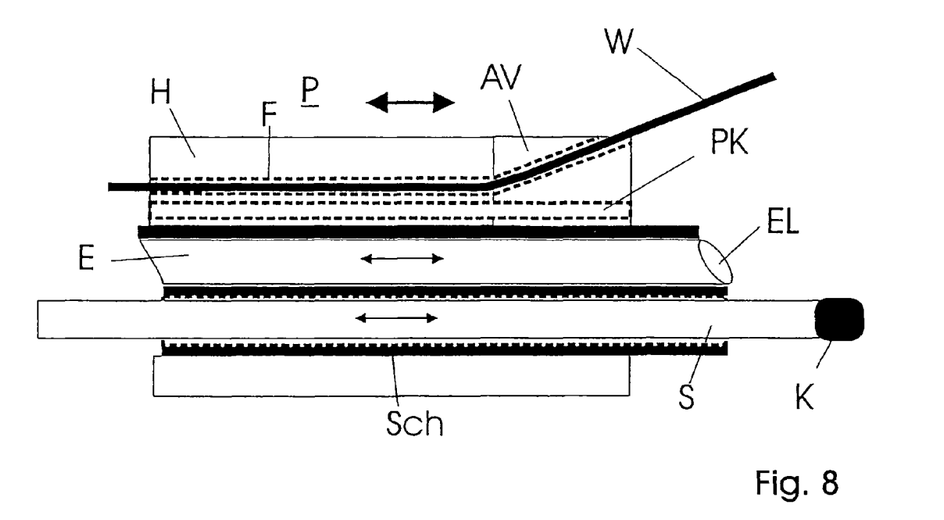
Figure 9:
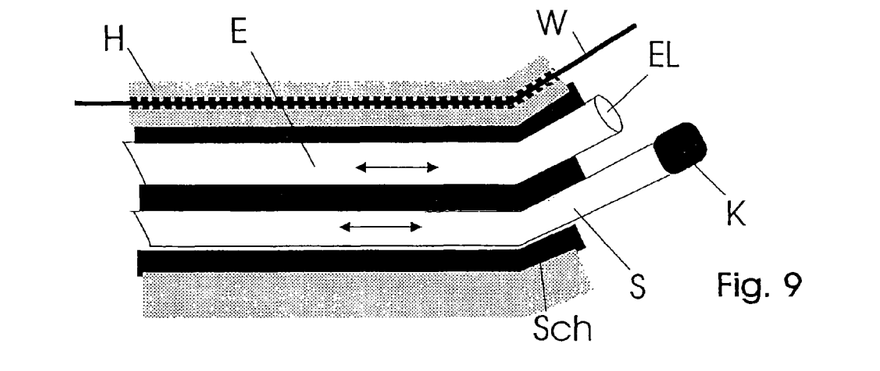

Modifications of the structure shown in FIG. 7 are illustrated in FIGS. 8 and 9. According to FIG. 8, a shaft Sch with two working channels is provided, in which, respectively, an ultrasonic probe with a sonic head K and an endoscope device E with an endoscope lens EL are arranged axially displaceably (double arrow). On the shaft Sch, an attachment sleeve H is attached on the outside, which forms a separate component that can be separated from the shaft Sch. The attachment sleeve H forms a positioning device P with a deflecting device AV for the tool W, which is arranged in a punction guide F. In the attachment sleeve, the perfusion channel PK is also arranged. The attachment sleeve extends preferably over the entire length of the shaft Sch, so that the end of the tool W is arranged in the area of the observation field of the examination devices in the working channels. The positioning apparatus P is connected releasably with the shaft.

With the use of flexible examination probes, the shaft Sch also can be angled (see FIG. 9). The attachment sleeve H, which preferably comprises an elastically deformable plastic material, is correspondingly adapted.

Figure 10:
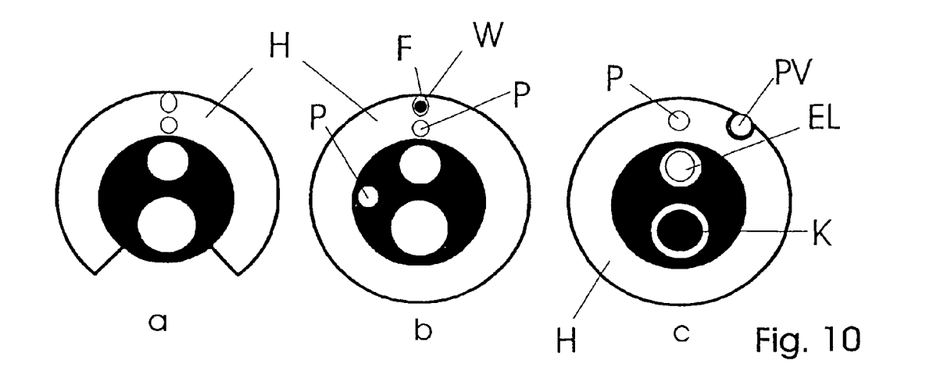
FIG. 10 shows schematic sectional views of embodiments of medical implements, according to the invention.

FIG. 10 illustrates the arrangement of the attachment sleeve H on the shaft Sch. The attachment sleeve H can surround the shaft Sch partially (FIG. 10a) or completely (FIGS. 10b, c). In the first case, the possibility of a radially transverse attachment of the attachment sleeve H is provided, while in the other cases, an axial shunting is necessary. In the shaft Sch, at least two working channels are provided. The attachment sleeve H contains the perfusion channel P and the functional guide F with the tool W. An additional perfusion channel P can also be provided in the shaft Sch (FIG. 10c). The attachment sleeve H can be equipped with outwardly open channels, depending on the use, in which at least one additional perfusion device PV can be inserted. The perfusion device PV is provided, in particular, for a radial spraying of the area in the organism, in which the implement is inserted. The perfusion device PV forms, for example, a removable catheter, which runs in a U-shaped depression in the attachment sleeve H or also in the shaft of the implement.

The attachment sleeve H can be displaced on the shaft Sch and/or rotated, in particular, in order to exactly orient the tool W.

The features of the invention in the foregoing description, in the claims, and in the drawings can be significant individually as well as also in combinations for the implementation of the invention in its various embodiments.

The invention claimed is:

1. A positioning apparatus for at least one examination probe comprising:
a rigid shaft having at least one working channel for receiving an examination probe, said rigid shaft having first and second ends and an outer major side surface therebetween and a shaft axis;
a puncture guide attached on the outer major side surface of the shaft, the puncture guide having at least one tube-shaped lumen for receiving an examination or operating device; and
a deflecting device attached on the outer major side surface of the shaft, wherein:
the lumen extends through the deflecting device, wherein an end of the lumen has a curved course relative to the shaft axis, so that the end of the lumen forms a predetermined deflecting angle with the shaft axis,
the lumen and the deflecting device can be displaced relative to the shaft at a predetermined distance parallel to the shaft axis, and
at least one of the lumen and the deflecting device is arranged for adjusting the examination or operating device in a predetermined manner with the deflecting angle relative to the shaft axis or for displacing the examination or operating device.

2. The positioning apparatus according to claim 1, in which the shaft contains a flushing perfusion channel, which opens near or in front of the end of the examination probe.

3. The positioning apparatus according to claim 1, wherein the shaft comprises an attachment sleeve which includes the puncture guide.

4. The positioning apparatus according to claim 3, in which the attachment sleeve is axially displaceable on the shaft at predetermined distances or corresponding predetermined coordinate values and is rotatably mounted and contains the deflecting device.

5. The positioning apparatus according to claim 3, in which the attachment sleeve can be attached transversely to the shaft.

6. The positioning apparatus according to claim 3, in which the attachment sleeve contains a flushing perfusion channel, which opens near or in front of the end of the examination probe.

7. The positioning apparatus according to claim 1, wherein the examination probe comprises an ultrasound, MRI, or endoscope probe.

8. The positioning apparatus of claim 1, wherein the lumen extends parallel to the shaft axis within the puncture guide.

9. The positioning apparatus of claim 1, wherein the deflecting device is formed integrally as part of the puncture guide.

10. The positioning apparatus of claim 9, wherein the lumen has first and second ends, both said first and second ends having a curved course relative to the shaft axis.

11. A positioning apparatus for at least one examination probe comprising:
a rigid shaft having at least one working channel for receiving an examination probe, said rigid shaft having a longitudinal shaft axis, first and second ends and an outer major side surface therebetween;
a puncture guide mounted on the outer major side surface of the rigid shaft, the puncture guide having at least one tube-shaped lumen for receiving an examination or operating device; and
a deflecting device mounted on the outer major side surface of the rigid shaft, wherein:
the lumen extends through the deflecting device, wherein an end of the lumen has a curved course relative to the longitudinal shaft axis, so that the end of the lumen forms a predetermined deflecting angle with the longitudinal shaft axis such that the end of the lumen is directed away from the shaft axis, the lumen and the deflecting device can be displaced relative to the rigid shaft at a predetermined distance parallel to the longitudinal shaft axis, and at least one of the lumen and the deflecting device is arranged for adjusting the examination or operating device in a predetermined manner with the deflecting angle relative to the longitudinal shaft axis or for displacing the examination or operating device.

12. The positioning apparatus according to claim 11, in which the rigid shaft contains a flushing perfusion channel, which opens near or in front of the end of the examination probe.

13. The positioning apparatus according to claim 11, wherein the rigid shaft comprises an attachment sleeve which includes the puncture guide.

14. The positioning apparatus according to claim 13, in which the attachment sleeve is axially displaceable on the rigid shaft at predetermined distances or corresponding predetermined coordinate values and is rotatably mounted and contains the deflecting device.

15. The positioning apparatus according to claim 13, in which the attachment sleeve is attached transversely to the rigid shaft.

16. The positioning apparatus according to claim 13, in which the attachment sleeve contains a flushing perfusion channel, which opens near or in front of the end of the examination probe.

17. The positioning apparatus according to claim 11, wherein the examination probe comprises an ultrasound, MRI, or endoscope probe.

18. The positioning apparatus according to claim 11, wherein the end of the lumen is within the deflecting device.

19. The positioning apparatus of claim 11, wherein the lumen extends parallel to the shaft axis within the puncture guide.

20. The positioning apparatus of claim 11, wherein the deflecting device is formed integrally as part of the puncture guide.

21. The positioning apparatus of claim 20, wherein the lumen has first and second ends, both said first and second ends having a curved course relative to the shaft axis.

* * * * *